US006670179B1

(12) United States Patent
Mattson et al.

(10) Patent No.: US 6,670,179 B1
(45) Date of Patent: Dec. 30, 2003

(54) MOLECULAR FUNCTIONALIZATION OF CARBON NANOTUBES AND USE AS SUBSTRATES FOR NEURONAL GROWTH

(75) Inventors: Mark P. Mattson, Bel Air, MD (US); Robert C. Haddon, Riverside, CA (US); Apparao M. Rao, Anderson, SC (US)

(73) Assignee: University of Kentucky Research Foundation, Lexington, KY (US)

( * ) Notice: Subject to any disclaimer, the term of this patent is extended or adjusted under 35 U.S.C. 154(b) by 11 days.

(21) Appl. No.: 09/920,213

(22) Filed: Aug. 1, 2001

(51) Int. Cl.$^7$ .................................................. C12N 5/00

(52) U.S. Cl. .................... 435/325; 435/325.1; 435/326; 435/398; 435/402

(58) Field of Search ........................ 424/93.7; 117/921; 423/460; 564/123; 435/325.1, 402, 326, 398, 325

(56) References Cited

U.S. PATENT DOCUMENTS

| | | | | |
|---|---|---|---|---|
| 5,092,871 A | * | 3/1992 | Aebischer et al. | 606/152 |
| 5,420,081 A | | 5/1995 | Mattes et al. | |
| 5,750,376 A | | 5/1998 | Weiss et al. | |
| 5,830,539 A | | 11/1998 | Yan et al. | |
| 5,851,832 A | | 12/1998 | Weiss et al. | |
| 5,958,875 A | | 9/1999 | Longo et al. | |
| 5,980,885 A | | 11/1999 | Weiss et al. | |
| 6,071,889 A | | 6/2000 | Weiss et al. | |
| 6,497,729 B1 | * | 12/2002 | Moussy et al. | 623/23.57 |
| 2002/0111694 A1 | * | 8/2002 | Ellingsen et al. | 623/23.57 |
| 2003/0032946 A1 | * | 2/2003 | Fishmann et al. | 604/890.1 |
| 2003/0040112 A1 | * | 2/2003 | Muir | 435/368 |
| 2003/0113714 A1 | * | 6/2003 | Belcher et al. | 435/5 |

OTHER PUBLICATIONS

Rao (1999) "Multipotent and Restricted Precursors in the Central Nervous System." The Anatomical Record (New Anat.) 257: 137–148.*

Kandel et al. (2002) Principles of Neural Science Chapter 4: "The Cytology of Neurons" pp. 67–87.*

Neet & Campenot (Jul. 2001) "Receptor binding, internalization, and retrograde transport of neurotrophic factors." Cell. Mol. Life Sci. 58(8): 1021–1035.*

Kandel et al. Principles of Neural Science Chapter 15: "Neurotransmitters" pp. 280–297 (2002).*

Goldsby et al. (2000) Kuby Immunology $4^{th}$ Ed. Chapter 12: "Cytokines" pp. 303–327.*

Bikfalvi et al. (1997) "Biological Roles of Fibroblast Growth Factor–2." Endocrine Reviews 18(1): 26–45.*

Grill et al. (2000) "Neuroprosthetic Applications of Electrical Stimulation." Asst. Technology 12(1): 6–20.*

Payne et al. (Aug. 1992) "repair and Regeneration: Experimental Aspects of Spinal Cord Disease." Current Opinion in Neurology and Neurosurgery 5(4): 558–62.*

Heidushka & Thanos (1998) "Implantable Bioelectronic Interfaces for Lost Nerve Functions." Progress in Neurobiology 55(5): 433–461.*

(List continued on next page.)

*Primary Examiner*—Gary Kunz
*Assistant Examiner*—Christopher James Nichols
(74) *Attorney, Agent, or Firm*—King & Schickli, PLLC

(57) ABSTRACT

A cell and substrate system and nerve regeneration implant are disclosed including a carbon nanotube and a neuron growing on the carbon nanotube. Both unfunctionalized carbon nanotubes and carbon nanotubes functionalized with a neuronal growth promoting agent may be utilized in the invention. A method is also disclosed for promoting neuronal growth.

7 Claims, 2 Drawing Sheets

OTHER PUBLICATIONS

Ravindran et al. (Mar. 23–37, 2003) "Neural network on patterned carbon nanotubes substrate." Abstracts of Papers 225th AC National Meeting, New Orleans, LA. (pp. IEC–160).*

Andrews R., Jacques D., Rao A.M., Derbyshire F., Qian D., Fan X., Et Al., Continuous production of aligned carbon nanOtubes: a step closer to commerical realization. Chemcial Physics Letters 303 (1999) pp. 467–474. Elsevier Science B.V.

Mattson, Mark P., Neurotransmitters in the regulation of neuronal cytoarchitecture. Brain Research Reviews, 13 (1988) pp. 179–212. Elsevier Science.

Waeg G., Dimsity G. and Esterbauer H., Monoclonal Antibodies for Detection of 4–Hydroxynonenal Modified Proteins. Free Rad. Res., vol. 25, No. 2, pp. 149–159. Overseas Publishers Association 1996.

Mattson M.P., Weiming F., Waeg G. and Uchida K., 4–Hydroxynonenal, a product of lipid peroxidation, inhibits dephosphorylation of the microtubule–associated protein tau. NeuroReports, vol. 8, No. 9–10 pp. 2275–2281 (Jul. 7, 1997). Rapid Science.

Kater S.B., Mattson Mark P., Cohan Christopher, and Connor John, Calcium regulation of the neuronal growth cone. Trends Neurosci., vol. 11, No. 77 (1988). Elsevier Publications, Cambridge.

Mark R.J., Lovell M.A., Markesbery W.R., Uchida K. and Mattson M.P., A Role for 4–Hydroxynonenal, an Aldehydic Product of Lipid Peroxidation, in Disruption of Ion Homeostatis and Neuronal Death Induced by Amyloid B–Peptide, J., (1997).

Carini R., Bellomo G., Paradisi L., Dianzani M. and Albano E., 4–Hydroxynonenal Triggers Ca2+ Influx in Isolated Rat Hepatocytes. Biochem. Biophys. Res. Commun. 218, 772–776 (1996). Academic Press, Inc.

Mattson, Mark P., Haddon, Robert C. and Rao, Apparao M., Molecular Functionalization of Carbon Nanotubes and Use as Substrates for Neuronal Growth. Journal of Molecular Neuroscience vol. 14, pp. 175–182 (2000). Humana Press Inc.

* cited by examiner

MOLECULAR FUNCTIONALIZATION OF CARBON NANOTUBES AND USE AS SUBSTRATES FOR NEURONAL GROWTH

TECHNICAL FIELD

The present invention relates generally to the fields of carbon nanotube technology and neurobiology and, more particularly, to a cell and substrate system or nerve regeneration implant and to a method for promoting neuronal growth.

BACKGROUND OF THE INVENTION

The mammalian nervous system is a complex cellular communication network that contains over $10^{11}$ nerve cells or neurons. Each of these neurons has an elaborate morphology including axons and dendrites that extend over long distances. These axons and dendrites are collectively known as neurites. Synapses are the point at which a nervous impulse passes from one neuron to another. The growth of neurites and the formation of synapses during development and regeneration is controlled by highly motile structural specialization at the tip of the neurite called the growth cone. Our ability to develop advances in technology to allow better regeneration and restoring of function of damaged neuronal circuits will first require a heightened understanding of growth cone physiology.

Presently the studying of mechanisms that regulate neurite outgrowth generally employ cultures of disassociated neurons from brains or spinal cords of embryonic rodents. Specifically, the neurons are seeded into dishes having a culture surface that has been coated with a uniform layer of adhesive molecules that promote neurite outgrowth. Although studies using this approach have led to the identification of a number of molecules that promote or inhibit neurite outgrowth, this approach does not allow for the manipulating of the growth environment at the nanometer scale. Accordingly, many mysteries of the growth mechanism remain.

A need is therefore identified for a means of studying neurite outgrowth at the nanometer scale. The present invention relates to a cell and substrate system and a method for promoting neuronal growth which will allow completion of these studies as well as to an implant for effectively promoting nerve regeneration.

SUMMARY OF THE INVENTION

In accordance with the purposes of the present invention as described herein, a cell and substrate system or nerve regeneration implant is provided. This system/implant comprises a carbon nanotube and a neuron growing on that carbon nanotube.

The carbon nanotube has a diameter of about 1.0–100.0 nm and a length of between about 20–100 µm. In one embodiment the carbon nanotube is functionalized with a neuronal growth promoting agent. That neuronal growth promoting agent may be selected from a group consisting of 4-hydroxynonenal, acetylcholine, dopamine, GABA (g-aminobutyric acid), glutamate, serotonin, somatostatin, nitrins, semaphorins, roundabout, calcium ($Ca^{2+}$) mixtures thereof.

In accordance with yet another aspect of the present invention a method is provided for promoting neuronal growth. That method may be broadly described as including the step of growing a neuron on a carbon nanotube.

In accordance with one embodiment of the invention the method may include the step of functionalizing the carbon nanotube with a neuronal growth promoting agent. That agent may be selected from a group consisting of 4-hydroxynonenal, acetylcholine, dopamine, GABA (g-aminobutyric acid), glutamate, serotonin, somatostatin, nitrins, semaphorins, roundabout, calcium ($Ca^{2+}$) mixtures thereof.

The functionalizing step may include the step of sonicating the carbon nanotubes in an acid solution containing the neuronal growth promoting agent.

The method further includes the step of applying the functionalized carbon nanotube to a glass coverslip. This is followed by the placing of the glass coverslip and attached functionalized carbon nanotube in a culture dish with a culture medium suitable for supporting the growth of neuronal cells. This is followed by the seeding of a neuronal cell into the culture dish.

The benefits and advantages of the present invention will become readily apparent to those skilled in this art from the following description wherein there is shown and described preferred embodiments of this invention, simply by way of illustration of various modes best suited to carry out the invention. As it will be realized, the invention is capable of other different embodiments, and its several details are capable of modification in various, obvious aspects all without departing from the invention. Accordingly, the drawing and descriptions will be regarded as illustrative in nature and not as restrictive.

BRIEF DESCRIPTION OF THE DRAWING

The accompanying drawing incorporated in and forming a part of this specification, illustrates several aspects of the present invention, and together with the description serves to explain the principles of the invention. In the drawing.

Reference will now be made in detail to the present preferred embodiment of the invention, an example of which is illustrated in the accompanying drawing.

DETAILED DESCRIPTION OF THE INVENTION

The present invention relates to a cell and substrate system or a nerve regeneration implant comprising a carbon nanotube 10 and a neuron 12 growing on that carbon nanotube. Typically carbon nanotubes 10 utilized in the present invention have a diameter of about 1.0–100.0 nm and a length of between about 20–100 µm.

In accordance with an additional aspect of the present invention, the carbon nanotube 10 may be functionalized with a neuronal growth promoting agent. The neuronal growth promoting agent may be selected from a group consisting of 4-hydroxynonenal, acetylcholine, dopamine, GABA (g-aminobutyric acid), glutamate, serotonin, somatostatin, nitrins, semaphorins, roundabout, calcium ($Ca^{2+}$) mixtures thereof.

Figure 1:
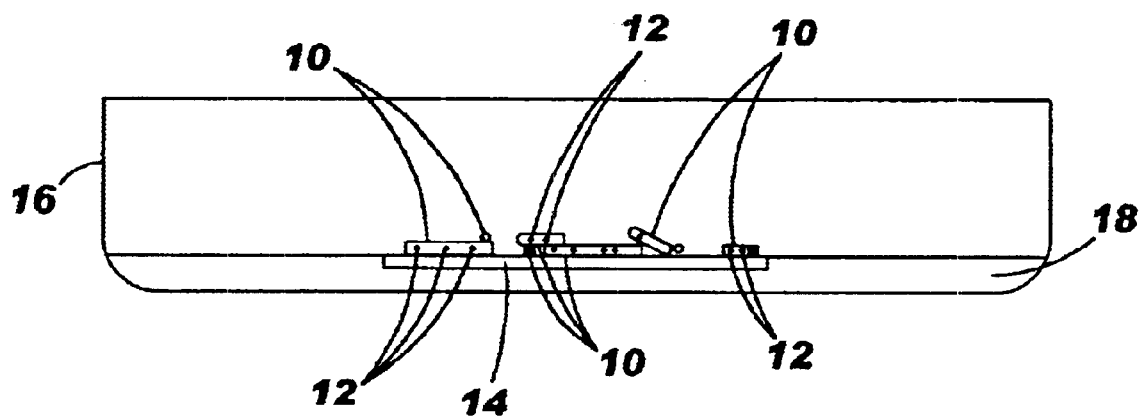
FIG. 1 is a schematical illustration showing a group of neuronal cells growing on some carbon nanotubes attached to a glass coverslip held in a culture dish with a culture medium.

Reference will now be made to FIG. 1 which illustrates the method of the present invention for promoting neuronal growth. That method may be broadly defined as including the step of growing a neuron 12 on a carbon nanotube 10. In accordance with a further aspect of the present invention the method may incorporate the step of functionalizing that carbon nanotube 10 with a neuronal growth promoting agent such as 4-hydroxynonenal, acetylcholine, dopamine, GABA (g-aminobutyric acid), glutamate, serotonin, somatostatin, nitrins, semaphorins, roundabout, calcium ($Ca^{2+}$) mixtures thereof.

More specifically describing the invention, multiwalled nanotubes 10 are synthesized in accordance with any appropriate method known in the art such as via catalytic decomposition of a ferrocene-xylene mixture. (Andrews R., Jacques D., Rao A. M., Derbyshire F., Qian D., Fan X., et al. (1999) Continuous production of aligned carbon nanotubes: a step closer to commercial realization. *Chem. Phys. Lett.* 303, 467). The nanotubes 10 are sonicated in a bath of 100% ethanol or other appropriate solvent and the dispersed nanotubes are then applied to glass coverslips 14 that are coated with a thin layer of polyethyleneimine or other appropriate neuronal growth promoting agent. The ethanol is then allowed to evaporate under ambient conditions. This serves to formally adhere the carbon nanotubes 10 to the coverslips 14. The coverslips 14 are then placed into plastic culture dishes 16. The coverslips 14 and dishes 16 are then sterilized by any appropriate means such as 5-minute exposure to UV light and an appropriate culture medium 18 is added to the dishes.

Next is the seeding of neuronal cells in the culture dish. The neurons 12 may then be grown in the culture dish 16 on the carbon nanotubes 10 for up to eight or more days since the nanotubes support long-term cell survival.

Neurons 12 grown on unfunctionalized carbon nanotubes 10 permit neurite outgrowth and the carbon nanotubes do not appear to influence the direction of the growth. The neurites tend to grow straight across the surfaces of the carbon nanotubes arranged in various orientations with respect to the direction of neurite outgrowth. Where neurites grew across carbon nanotubes 10 and then on to the polyethyleneimine coated glass coverslips 14, the neurites typically do not form branches on the nanotubes but did form branches on the coverslips. Thus, neurites grown on unfunctionalized carbon nanotubes 10 tend to be relatively unconducive to branch formation.

In order to grow neurons 12 with enhanced neurite branching and total neurite outgrowth, the carbon nanotubes 10 may first be functionalized with a neuronal growth promoting agent such as 4-hydroxynonenal, acetylcholine, dopamine, GABA (g-aminobutyric acid), glutamate, serotonin, somatostatin, nitrins, semaphorins, roundabout, calcium ($Ca^{2+}$) mixtures thereof.

Toward this end, the carbon nanotubes 10 may be initially dispersed by sonification in 100% ethanol. The dispersed carbon nanotubes 10 are then incubated in an acidic solution, approximate pH 5.0, of 50% ethanol at a concentration of, for example, 4 mg of carbon nanotubes per mL containing the neuronal growth promoting agent. The mixture is sonicated for an appropriate time (e.g. 20 min.) in a bath sonicator and the carbon nanotubes 10 are then recovered and applied to glass coverslips 14 coated with polyethyleneimine, a substrate for neuronal growth. The coverslips 14 are then washed extensively with, for example, a phosphate-buffered saline, sterilized such as by exposure to UV light for, for example, five minutes, and placed in culture dishes 16 containing an appropriate culture medium 18.

This is followed by the seeding of the glass coverslips 14 in the culture dish with neuronal cells 12. The neuronal cells 12 are then grown on the functionalized carbon nanotubes 10 for eight or more days in culture. The resulting product may be used as a cell and substrate system for the study of neurons and particularly the growth cone of neurons 12 at the nanometer scale or even as a nerve regeneration implant. In addition, since carbon nanotubes 10 are excellent electrical conductors, the cell and substrate system of the present invention is expected to prove valuable for electrophysiological analyses of neuronal microcircuitry.

More specifically, carbon nanotubes of defined diameters ranging from 1 nm to 100 nm may now be routinely produced. These diameters are similar to those of small nerve fibers, growth cone filopodia and synaptic contacts. Accordingly, neurons grown on carbon nanotubes encounter an environment that resembles in some way cell surfaces and extra-cellular matrix structures that neurons encounter in vivo. Thus, it is believed that the nerve regeneration implants of the present invention will be particularly useful and effective in regenerating and/or restoring the function of damaged neuronal circuits.

The following example is presented to further illustrate the invention, but it is not to be considered as limited thereto. In the examples, the multiwalled carbon nanotubes utilized were synthesized via the catalytic decomposition of a ferrocene-xylene mixture as described in the article entitled "Continuous Production of Aligned Carbon Nanotubes: A Step Closer to Commercial Realization" by Andrews et al. noted above. The primary hippocampal cell cultures utilized were established from E18 rat embryos using methods described previously. (Mattson M. P. (1988) Neurotransmitters in the regulation of neuronal cytoarchitecture. *Brain Res. Rev.* 13, 179–212). The multi-walled carbon nanotubes utilized in the examples had diameters of approximately 20 nm and lengths of 20–100 $\mu$M. These carbon nanotubes were produced as sheets in which the nanotubes were arranged in parallel array.

The dissociated cells were seeded onto polyethyleneimine-coated 22 $mm^2$ glass coverslips and incubated in neurobasal medium containing B-27 supplements (Gibco-BRL) plus 2 mM L-glutamine, 1 mM HEPES, and 0.001% gentamicin sulfate (Sigma).

All cultures in the example were examined and photographed using a light microscope with phase-contrast optics and some of the cultures were prepared for examination with a scanning electron microscope (SEM).

Unfunctionalized carbon nanotubes were dispersed by bath sonication for 5 min in 100% ethanol. The dispersed nanotubes were applied to 22 $mm^2$ glass coverslips that had been coated with a thin layer of polyethyleneimine. The ethanol was allowed to evaporate under ambient conditions, resulting in firm adherence of the nanotubes to the coverslips. The coverslips were then placed in 33-mm diameter plastic-culture dishes, sterilized by a 5-min exposure to UV light, and culture medium was added to the dishes. The next day dissociated embryonic rat hippocampal neurons were seeded into the cultures. Adhesion of 4-hydroxynonenal ( 4-HNE) to nanotubes was accomplished by first dispersing the nanotubes in 100% ethanol, and then incubating the dispersed nanotubes in an acidic solution, pH 5.0, of 50% ethanol (4 mg nanotubes/mL) containing 200 $\mu$M 4-HNE (Cayman Chemical Co.). The mixture was then sonicated for 20 min in a bath sonicator, and nanotubes were applied to polyethyleneimine-coated glass coverslips. The coverslips were then washed extensively with phosphate-buffered saline (PBS), sterilized by exposure to UV light for 5 min, and placed in culture dishes containing medium.

In order to determine whether 4-HNE was bound to the nanotubes, an antibody against 4-HNE was employed. (Waeg G., Dimsity G., and Esterbauer H. (1996) Monoclonal antibodies for detection of 4-hydroxynonenal modified proteins. *Free Rad. Res.* 25, 149–159; Mattson M. P., Fu W., Waeg G., and Uchida K. (1997) 4-hydroxynonenal, a product of lipid peroxidation, inhibits dephosphorylation of the microtubule-associated protein tau. *NeuroReport* 8, 2275–2281.) Examination of the nanotubes using confocal laser-scanning microscopy and SEM showed that 4-HNE antibody bound strongly to the nanotubes that had been reacted with 4-HNE; but not to untreated nanotubes or to nanotubes reacted with 4-HNE that had been preincubated with a 100-fold molar excess of histidine. 4-HNE was present along the length of the nanotubes. These findings demonstrate a physical association of 4-HNE with the nanotubes under the conditions employed.

Figure 2:
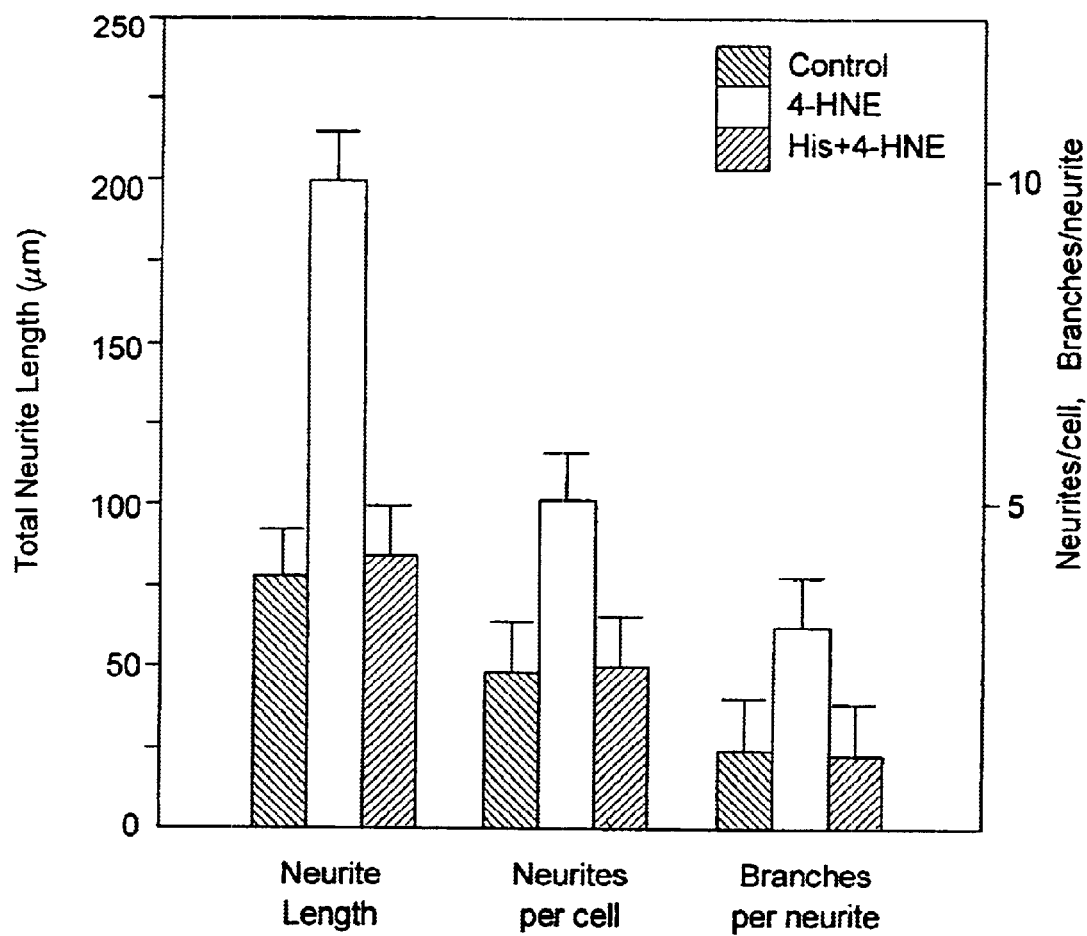
FIG. 2 is a graphical illustration showing the numbers of neurites/neuron, total neurite length/neuron and numbers of branches/neurite in neurons grown on carbon nanotubes coated with 4-hydroxynonenal and neurons grown on control nanotubes without any functionalization and nanotubes reacted with 4-hydroxynonenal that had been pre-incubated with a 100-fold molar excess of histidine.

We next cultured embryonic hippocampal neurons on nanotubes coated with 4-HNE, and on control nanotubes that were either untreated or reacted with 4-HNE that had been preadsorbed with excess histidine. SEM examination suggested that neurons grown on nanotubes modified with 4-HNE had more elaborate neuritic arbors than did neurons grown on unmodified nanotubes. We therefore quantified numbers of neurites/neuron, total neurite length/neuron, and numbers of branches/neurite in neurons grown on nanotubes coated with 4-HNE, and neurons grown on control nanotubes (See FIG. 2). Whereas neurons grown on control nanotubes possessed only one or two neurites, those grown on 4-HNE-modified nanotubes elaborated 4–6 neurites. Total neurite length was increased more than twofold, and number of branches/neurite were increased approximately threefold, in neurons grown on 4-HNE-modified nanotubes. These findings demonstrate a striking effect of nanotube-bound 4-HNE on neurite outgrowth, and establish the feasibility of using chemically modified carbon nanotubes as a tool for studying and manipulating neurite outgrowth.

These findings suggest the possibility that 4-HNE enhances adhesion of growth cones to the nanotubes. Previous studies have shown that $Ca^{2+}$ influx can regulate growth cone motility and neurite elongation (Kater S. B., Mattson M. P., Cohan C., and Connor J. (1988) Calcium regulation of the neuronal growth cone. *Trends Neurosci.* 11, 315–321), and that 4-HNE can modulate intracellular $Ca^{2+}$ levels in cultured hippocampal neurons (Mark R. J., Lovell M. A., Markesbery W. R., Uchida K., and Mattson M. P. (1997) A role for 4-hydroxynonenal in disruption of ion homeostasis and neuronal death induced by amyloid β-peptide. *J. Neurochem.* 68, 255–264) as well as in non-neuronal cells (Carini R., Bellomo G., Paradisi L., Dianzani M. U., and Albano E. (1996) 4-Hydroxynonenal triggers $Ca^{2+}$ influx in isolated rat hepatocytes. *Biochem. Biophys. Res. Commun.* 18, 772–776). It is therefore possible that the neurite outgrowth-enhancing effect of 4-HNE involves changes in intracellular $Ca^{2+}$ levels, although this remains to be established.

The foregoing description of the preferred embodiment of the invention has been presented for purposes of illustration and description. It is not intended to be exhaustive or to limit the invention to the precise form disclosed. Obvious modifications or variations are possible in light of the above teachings. For example, a carbon nanotube may be substituted for a neuron in vivo. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A cell and substrate system, comprising a carbon nanotube; and a mammalian embryonic hippocampal neuron growing on said carbon nanotube.

2. The system of claim 1, wherein said carbon nanotube has a diameter of about 1.0–100.0 nm.

3. The system of claim 2, wherein said carbon nanotube has a length of between about 20–100 μm.

4. The system of claim 1, wherein said carbon nanotube is functionalized with 4-hydroxynonenal.

5. A carbon nanotube functionalized with 4-hydroxynonenal.

6. The carbon nanotube of claim 5, wherein said carbon nanotube has a diameter of about 1.0–100.0 nm.

7. The carbon nanotube of claim 6, wherein said carbon nanotube has a length of between about 20–100 μm.

* * * * *